United States Patent [19]

Bagwell

[11] Patent Number: 4,767,576

[45] Date of Patent: Aug. 30, 1988

[54] NEBULIZER WITH AUXILIARY GAS INPUT

[75] Inventor: James T. Bagwell, Anaheim, Calif.

[73] Assignee: CIMCO, Costa Mesa, Calif.

[21] Appl. No.: 927,812

[22] Filed: Nov. 6, 1986

Related U.S. Application Data

[63] Continuation-in-part of Ser. No. 661,149, Oct. 15, 1984, Pat. No. 4,629,590.

[51] Int. Cl.⁴ .................. B01F 3/04; A61M 11/02
[52] U.S. Cl. .................... 261/16; 128/200.18; 128/200.21; 239/338; 261/78.2; 261/142; 261/DIG. 65
[58] Field of Search .......... 261/78.2, 79.2, 123, 261/141, 16, 142, 64.1, DIG. 65, DIG. 77; 220/378; 239/338; 215/200; 128/200.18, 200.21, 203.26, 203.27, 202.27, 204.17; 55/257 R, 257 PV; 219/271–276

[56] References Cited

U.S. PATENT DOCUMENTS

| | | | |
|---|---|---|---|
| 2,835,267 | 5/1958 | Andresen et al. | 261/78.2 X |
| 3,206,175 | 9/1965 | Boteler | 261/78.2 X |
| 3,353,536 | 11/1967 | Bird et al. | 128/200.18 |
| 3,527,411 | 9/1970 | Colgan | 239/338 |
| 3,724,454 | 4/1973 | Brown | 128/200.18 X |
| 3,744,771 | 7/1973 | Deaton | 261/78.2 |
| 3,836,079 | 9/1974 | Huston | 239/74 |
| 3,874,379 | 4/1975 | Enfield et al. | 128/200.18 |
| 4,007,238 | 2/1977 | Glenn | 261/78.2 |
| 4,039,639 | 8/1977 | Kankel et al. | 128/200.18 X |
| 4,101,611 | 7/1978 | Williams | 261/142 |
| 4,116,387 | 9/1978 | Kremer, Jr. et al. | 239/338 |
| 4,177,945 | 12/1979 | Schwartz et al. | 239/338 |
| 4,198,969 | 4/1980 | Virag | 261/78.2 X |
| 4,243,396 | 1/1981 | Cronenberg | 261/78.2 X |
| 4,267,974 | 5/1981 | Kienholz et al. | 239/74 |
| 4,299,355 | 11/1981 | Häkkinen | 239/338 |
| 4,427,004 | 1/1984 | Miller | 239/338 X |

Primary Examiner—Richard L. Chiesa
Attorney, Agent, or Firm—Gausewitz, Carr & Rothenberg

[57] ABSTRACT

A nebulizer has a mixing chamber into which is projected a high velocity jet of oxygen that aspirates water from a container connected with the mixing chamber. A compressed air input port in the chamber projects a stream of compressed air adjacent to and alongside the oxygen jet to impinge upon the tapered entrance surface of a venturi tube that forms an exit from the mixing chamber. The percentage of oxygen in the output is effectively rendered independent of output back pressure, the lower limit of the amount of oxygen in the output is lowered, the amount of water entrained in the output is increased, and the amount of waste water is decreased.

4 Claims, 3 Drawing Sheets

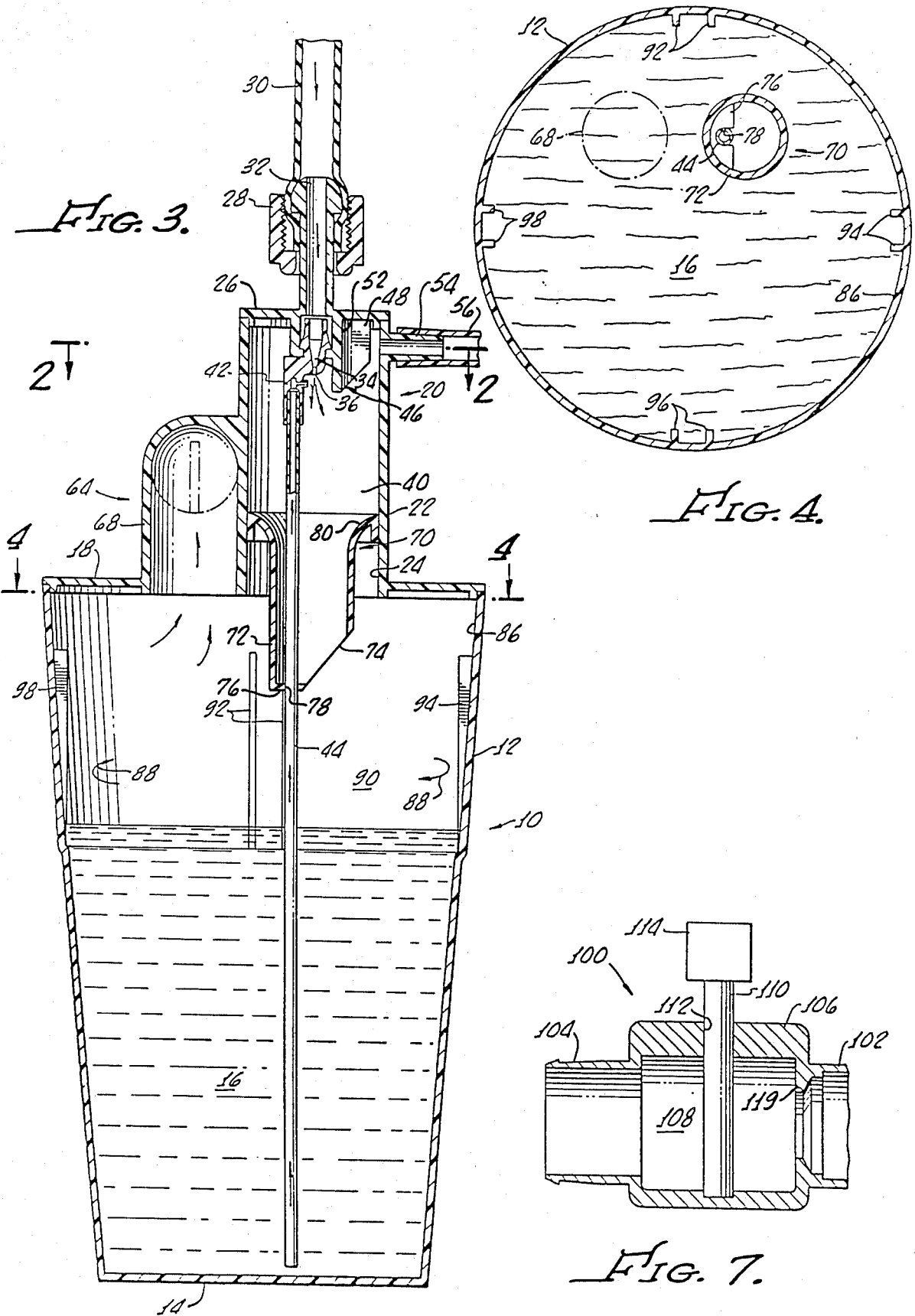

NEBULIZER WITH AUXILIARY GAS INPUT

This application is a continuation-in-part of my prior application for Nebulizer, Ser. No. 661,149, filed Oct. 15, 1984, now U.S. Pat. No. 4,629,590 issued 3-17-87 and assigned to the assignee of the present application.

BACKGROUND OF THE INVENTION

The present invention relates to nebulizers for inhalation therapy. It more particularly concerns a nebulizer having improved moisturizing capability with a wider range of oxygen percentage and less susceptibility to variation of back pressure.

In common forms of inhalation therapy, oxygen or an oxygen enriched mixture of air is provided for introduction to a patient's lungs by means of suitable breathing apparatus. The gas mixture is preferably moisturized and transmitted to the patient through a flexible tube which may be several feet or more in length. Particularly where such a tube is corrugated, but even where it is not, water in the moisturized gas mixture tends to drop out of the mixture, collecting in lower portions or bends of the connecting conduit. The water collected in the conduit may increase in volume to a point where the connecting conduit is either partially or entirely blocked, thereby greatly endangering the patient by obstruction of the supply of breathable gas.

The nebulizer provides a gas stream that entrains water particles rather than water vapor (as in a humidifier). It requires a minimum water particle size because it must insure that water particles will reach deeper portions of the respiratory tract. In a humidifier the gas carries water vapor rather than water particles and the moisture in the inhaled mixture may be absorbed before it reaches deeper portions of the respiratory tract. In the nebulizer, liquid particle size preferably is from about five microns down to about two microns. Particles larger than five microns have a greatly increased tendency to drop out of the mixture during flow from the nebulizer to the patient. It is these large size particles that must be avoided. Thus, large particles in the mixture do no good to the patient because they generally do not remain in the mixture for time long enough to reach the patient. But more importantly, they tend to collect and fully or partially occlude the connecting tubing, requiring frequent attention and draining of the tubing to avoid complete blocking of flow.

Prior attempts to remove larger droplets from the inhalation mixture are basically ineffective, inefficient, complex, and costly. For example, the U.S. Pat. No. to Cronenberg, 4,243,396, describes a tortuous spiral path formed between a pair of telescoping tubes as a separator of gas droplets. The U.S. Pat. No. to Kienholz et al, 4,267,974, describes a chamber which is termed a baffling chamber having a baffle plate at the chamber exit. The U.S. Pat. No. to Schwartz et al, 4,177,945, shows a tortuous path that results in turbulent flow for removal of liquid droplets. These arrangements are largely ineffective, greatly complicating nebulizer structure, thereby increasing costs and compromising efficiency.

Prior nebulizers have other problems, such as limited range of oxygen content of the output mixture and sensitivity to back pressure, which derive from the nature of their use and operational structure.

A nebulizer is used to provide a gas mixture that may be selectively varied from a high oxygen content to as little as 28% oxygen. Thus, the nebulizer is often provided with an adjustable air intake through which selectively varying amounts of air are admitted to the mixing chamber for mixing with the pure oxygen that is supplied under pressure.

Because air is generally drawn into the mixing chamber of the nebulizer by venturi action of a high-velocity oxygen stream, which provides the low pressure for drawing the air in, the minimum amount of oxygen percentage in the outgoing mixture is limited. Air itself has an oxygen content of about 21%, and thus it is not possible, by the negative pressure of venturi action of a stream of pure oxygen, to draw in enough air to obtain an oxygen content in the output of the nebulizer below 28%, as is often required or desired. Many nebulizers are not capable of providing an outgoing mixture having an oxygen content of less than about 35%, and oxygen content of less than about 28% has been available previously only with expensive and complex additional regulating equipment.

Normally, a nebulizer is adjusted to provide a desired predetermined oxygen flow rate, such as, for example, in the order of about five liters per minute, to thereby provide a desired output flow rate of the moisturized oxygen-enriched inhalation mixture of 28% oxygen. However, back pressure of various devices, including the patient mask and hoses interconnected between the mask and the nebulizer, will cause variation of the air entrainment input flow rate from a desired value, which, in turn, causes variation in the percentage of oxygen in the output mixture. Thus, outputs of prior nebulizers have been difficult to precisely control. Still further, the large droplets of water which fall out in the tubing connecting the nebulizer with the patient are waste, in addition to providing undesirable collections of water in the tubing, and generally indicate an inefficiency of complete utilization of the sterile water that is used.

Accordingly, it is an object of the present invention to provide a nebulizer that avoids or minimizes above mentioned disadvantages.

SUMMARY OF THE INVENTION

In carrying out principles of the present invention in accordance with a preferred embodiment thereof, a nebulizer for producing an output mixture of oxygen-enriched air and water for inhalation therapy comprises a container confining a body of liquid, a mixer body mounted to the container and defining a mixing chamber having a first input port, a nozzle in the chamber for projecting a first stream of gas at high velocity from the input port to the container, and aspirating means connected between a lower portion of the container and a point adjacent the nozzle for flowing water from the container to the gas stream. A second input port is provided in the chamber for projecting a second stream of a second gas toward the first stream to produce a combined stream comprising a mixture of water and gas from both of the input ports. More specifically, oxygen is projected as a first stream through a high velocity nozzle to entrain water from the container and to flow at high velocity through a venturi tube which couples the mixing chamber to an upper portion of the container, above the water confined therein. Compressed air is projected as a second gas into the chamber from the second input port and caused to flow alongside the high velocity oxygen stream and also toward the venturi. This compressed air stream impinges upon the inclined entrance surface of the venturi tube to provide improved mixing action.

BRIEF DESCRIPTION OF THE DRAWINGS

FIG. 3 is a longitudinal section of the nebulizer taken on line 3—3 of FIG. 2;

FIG. 4 is a section taken on line 4—4 of FIG. 3;

FIG. 7 is a sectional view of the heater taken on line 7—7 of FIG. 2.

DETAILED DESCRIPTION

Figure 1:
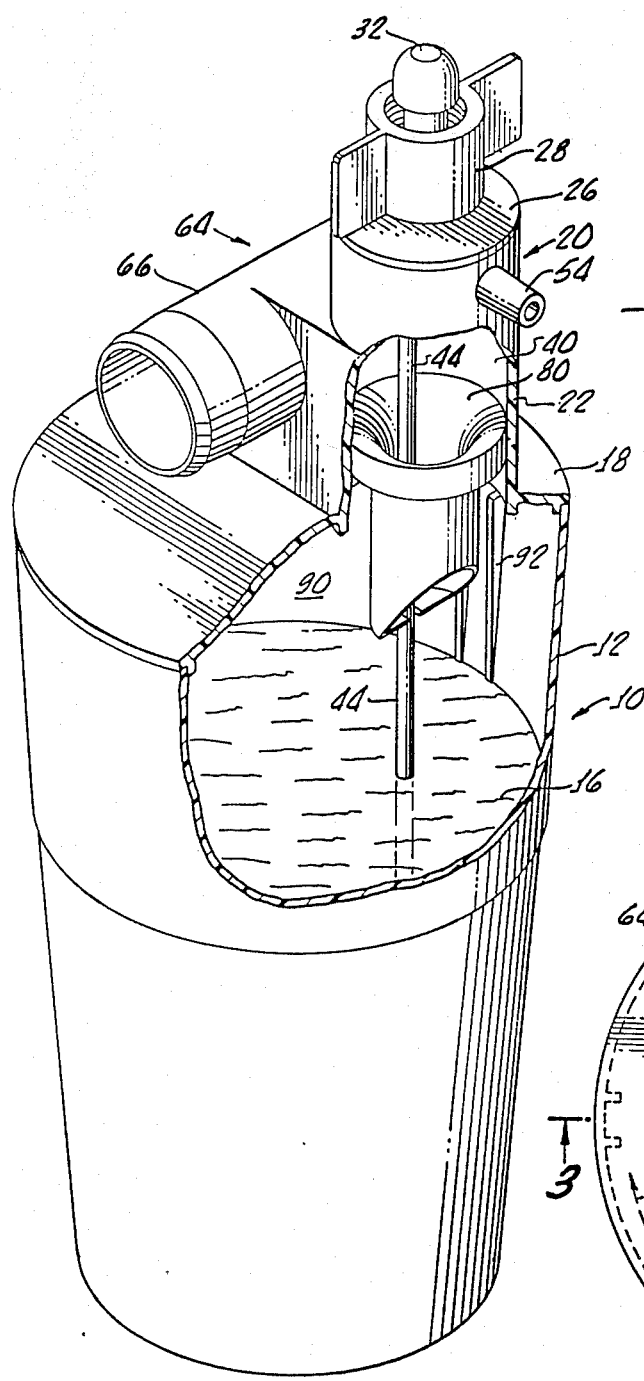
FIG. 1 is a pictorial illustration, with parts broken away, of a unitary nebulizer assembly incorporating features of the present invention.
Figure 2:
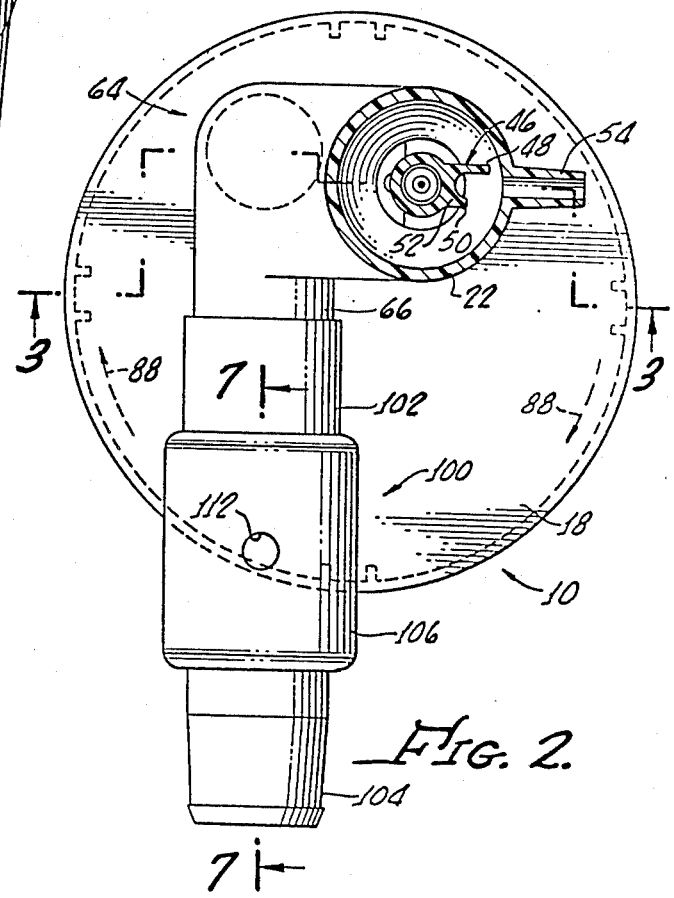
FIG. 2 is a section taken on line 2—2 of FIG. 3.

Shown in FIGS. 1 and 3 is a container 10 having a truncated conical wall 12 and a closed bottom 14 confining a body of liquid, such as sterilized water or a saline solution 16, filling the container to a point well below its upper edge. A lid 18 is fixed to and seals the open upper ends of the container and is molded integrally with a circular tubular mixture body 20 including a generally upstanding circular tubular wall 22 that extends from an opening 24 in the lid upwardly to a body cap 26 to which is secured an input fitting 28 connected to an input oxygen hose 30. Fixed to the cap 26, in line with the input passage 32 of the fitting 28, is a nozzle 34 having a nozzle discharge orifice 36 of decreased diameter, whereby the nozzle will project the incoming gas at high velocity into a mixing chamber 40 defined within the tubular mixer body 20. Mounted to and depending from the cap 26 is a liquid aspirating fitting 42 connected by means of a tube 44 to a lower portion of the container whereby the increased velocity gas projected from nozzle orifice 36 will provide a decreased pressure within the chamber at fitting 42 to draw liquid from the container to be mixed with the projected gas stream. Much of the liquid thus entrained within the increased velocity gas stream is in the form of water droplets, but many such droplets will be larger than the maximum desirable droplet size (about 5 microns).

Fixed to an depending from the cap 26, and also fixed to the exterior of nozzle 34 is a channel shaped baffle or air deflector 46 having first and second side walls 48,50 (FIG. 2) interconnected by a web 52 fixed to the body of nozzle 34. Wall 48 is significantly larger than wall 50, extending further from web 52 for reasons to be explained below. The lower end of deflector 46 extends somewhat below the orifice 36 and below the aspirating fitting 42.

A second gas input port in an upper portion of tubular wall 22 is defined by a fitting 54 sealed to wall 22 and having an axis normal to the axis of the circular wall 22 and directed at deflector web 52 at a point above nozzle orifice 36. The upper end of mixer body 20 is completely closed and sealed, except for the two gas input ports. Fitting 54 is connected via a hose 56 to a source of compressed air (not shown) to feed a stream of air to deflector 46. The latter redirects the air stream downwardly alongside the oxygen stream from nozzle 34 and along an axis substantially parallel to the axis of the oxygen stream but slightly skewed relative to the axis of the oxygen stream by virtue of the relatively extended deflector side wall 48. Thus the compressed air stream is directed downwardly with a component of circular motion. The mixer body is formed with an elbow conduit 64 having a horizontally directed nebulizer discharge or output leg 66 and a vertically directed leg 68 extending through the lid 18 into communication with the upper portion of container 10.

A mixture venturi tube 70 is fixed to and aligned with the tubular wall 22, extending downwardly therefrom in axial alignment with the input passage 32 and the axis of jet nozzle 34, through the lid 18, through the open end of mixer body 20, and terminating at an end 72 below the lid but adjacent the top of the container. Part of the wall of venturi tube 70 is cut away at the tube bottom as indicated at 74 to provide a laterally directed opening at the lower end of the venturi tube. This end of the venturi tube is partially blocked by a horizontal deflector plate 76 which is formed with a circular recess 78 through which extends the tube 44 for passage of liquid from the container to the mixing chamber 40. As can be seen in FIG. 3, tube 44 is offset slightly to the side of the nozzle orifice 36 so that the gas stream projected at increased velocity from the nozzle orifice and along the venturi tube axis will travel downwardly, expanding as it travels to partly impinge upon an upper curved and tapered entrance portion 80 of the venturi tube. The high velocity jet mixture is funneled by the venturi tube downwardly to its open end to impinge upon deflector 76 which redirects the jet stream outwardly from a point within the container at its upper portion to impinge upon the inner surface 86 of the container wall at an angle to the surface of this wall. The angular impingement of the redirected mixture upon the container wall again deflects the projected stream, redirecting the stream to flow circumferentially, in a generally horizontal plane, around the interior surface of the container 12 in the directions indicated by arrows 88 (FIG. 2).

The upper portion of container 12 between the lid and the upper surface of the liquid 16 defines a swirl chamber 90 into which the moisture entraining high velocity stream of oxygen enriched air is projected. The mixture is projected outwardly from a point within the swirl chamber and caused to flow in the described circumferential and substantially horizontal path. The mixture may begin to descend along the container walls in a downwardly spiral path as it swirls around the walls. Fixed to the inner surface of container wall 12 is a plurality of circumferentially spaced baffles 92, 94, 96 and 98 each of which extends vertically along the container sides. The baffles, in effect, form stiffening ribs for the container wall, but, because of their vertical extent across the horizontal direction of swirling mixture flow, primarily provide limited obstructions or obstacles to the circumferential flow of the mixture. Large water droplets entrained in the swirling gas mixture impinge upon the baffles in the course of the swirling flow of the mixture and are trapped, thereby to be removed from the swirling mixture and to flow downwardly along the container sides into the body of water within the container. The pressurized swirling mixture from the chamber 90 flows outwardly to be discharged from the container through discharge conduit 64.

An unexpectedly improved operation is achieved by the introduction of compressed air into mixing chamber 40. Fitting 54 directs a stream of compressed air horizontally into the mixing chamber and against deflector 46 which has a deflecting surface of web 52 curved in a circular arc, in a horizontal plane, as best seen in FIG. 2. The compressed air is redirected downwardly by the deflector, which, by virtue of the larger side wall 48, causes the downwardly deflected compressed air stream to flow almost entirely to one side of the deflector (toward the lower part of the drawing in FIG. 2). The compressed air stream is caused to flow toward the entrance surface of the venturi tube, with a slight swirling action which imparts to the gas a somewhat spiral, downward flow, tending to move around the mixing chamber in a clockwise direction as viewed in FIG. 2. This compressed air stream is substantially parallel to the oxygen stream from jet nozzle 36, but is transversely offset from the venturi tube axis so as to impinge upon the curved entrance surface 80 of the venturi tube and generate an increased turbulence in the mixing chamber 40. In the arrangement described herein the venturi tube 70 is fixed at a lower position with tubular mixer body as compared with the arrangement of my prior co-pending application, so as to provide a greater distance for the downwardly directed side by side flow of the moisture entraining oxygen stream and the compressed air stream.

The combined action of the liquid-entraining oxygen jet and the separately admitted jet of compressed air, which flows downwardly to the venturi tube alongside the oxygen jet, provides several surprising and unexpected improvements. It is found that entrainment of water in the discharged mixture is much greater with the described arrangement than in various arrangements of the prior art, and greater than in the apparatus described in the above-mentioned co-pending application. There is substantially less water drop out in the exit tubing, connecting the nebulizer to the patient, with the arrangement described herein. This significant improvement has been shown by comparative tests. In the prior arrangement of my copending application, 12% of the total water used (from the interior of the container) is found to collect in the tubing to the patient. With the arrangement described herein, on the other hand, where a separate compressed air input is provided, it is found that only 2½% of total water used collects in the output tubing. This is evidence of the significantly improved efficiency of moisture entrainment and of the desired increase in water content of the air supplied to the patient.

Another unexpected and surprising result derived in the operation of the invention described herein is that variation in back pressure does not significantly affect the percentage of oxygen in the output mixture. Further, the described arrangement enables independent control of the amount of water in the output mixture and the percentage of oxygen in the output mixture. The amount of water in the output mixture is controlled by control of the oxygen flow rate, which in turn controls water aspiration. The percentage of oxygen in the output mixture is controlled by varying flow rate of compressed air fed through the second input fitting 54. Still further, the amount of oxygen in the output can be controlled down to a small percentage, well below 28%, without expensive regulating valves or complex equipment. It is merely necessary to set the desired oxygen input flow rate at the desired level, such as, for example, five liters per minute, and then to open up a valve (not shown) on the input line 56 to the compressed air input fitting 54, thereby increasing air input and decreasing output oxygen percentage. In this connection, it may be noted that many hospital rooms are provided with fixtures on the wall from which are available hospital provided supplies of both oxygen and compressed air. Accordingly, it is a simple task to employ the nebulizer described herein, since one has only to connect suitable tubing between the oxygen and air input fittings of the nebulier and the output wall fittings of the hospital room.

Using a separate source of compressed air, an increased restriction or increased back pressure down not increase the percentage of oxygen in the output. Having a relatively large fixed pressure air supply fed to the compressed air input fitting 54, the percentage of oxygen in the output is independent of change in back pressure, so that when back pressure is increased, as by connection of the patient and/or tubing to the nebulizer, the percentage of oxygen in the output does not change. The compressed air may be fed to the input fitting 54 through a suitable filter or filters (not shown), as desired.

Figure 5:
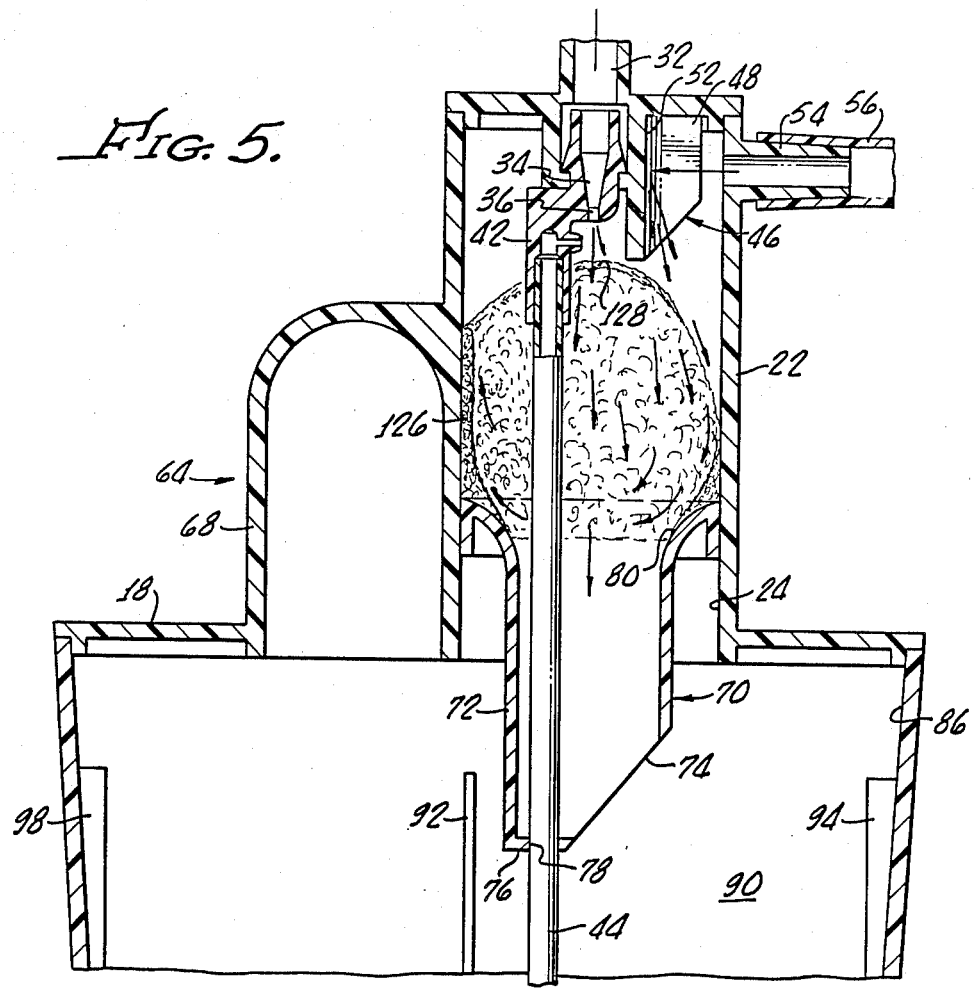
FIG. 5 is a vertical sectional view illustrating interaction of the two gas streams.
Figure 6:
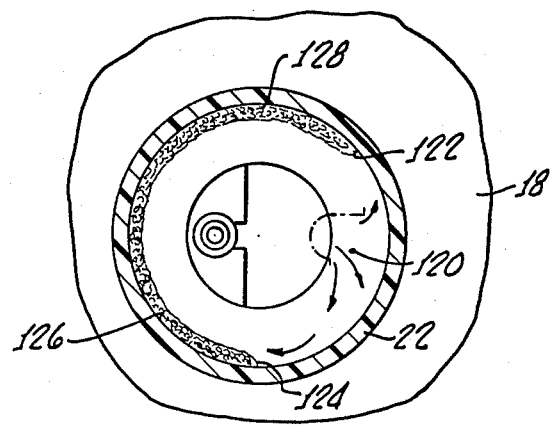
FIG. 6 is a horizontal sectional view showing the top of the venturi tube entrance surface and the flow of the gas-water mixture.

In the arrangement of my prior co-pending application, larger water particles forming in the mixing chamber fall downwardly into the chamber 90 of the container. With the present arrangement, on the other hand, such large particles are blown downwardly against the entrance surface of the venturi tube. These larger particles collect and are temporarily trapped on the entrance surface of the venturi tube, forming a body of exceedingly turbulent, "standing" water having a configuration as generally indicated in the schematic drawings of FIGS. 5 and 6. Thus, an area 120 is indicated in the horizontal sectional view of FIG. 6 as the center of impingement of the downwardly-directed compressed air stream upon the tapered entrance surface of the venturi tube. This center of impingement is laterally offset because of the configuration of deflector 46. Turbulence of the swirling air, oxygen and water mixture in the mixing chamber is greatly increased by the impingement of the compressed air jet upon the venturi tube entrance surface 80. Over a circumferential area of the venturi entrance surface extending in a clockwise direction from point 122 to point 124 there is relatively little "standing" water on the entrance surface. From point 124 clockwise toward point 122 there is built up around the interior of the tubular wall 22 a wall of turbulent "standing" water, generally indicated at 126, which has a height that increases from point 124 toward point 122. This wall of water is blown by the downwardly directed and somewhat skewed compressed air in a clockwise direction (as viewed in FIG. 6) and also upwardly along the wall 22 to a maximum height at a point, such as indicated at 128, where the wall of water appears to fall back downwardly upon itself. Thus, the compressed air jet creates and maintains a wall of turbulent water extending around a major part of the downwardly-projected oxygen jet, which wall of water, it is postulated, collects and holds larger water particles that tend to drop out of the high velocity oxygen stream and are too large to be fully entrapped in the oxygen stream.

As shown in FIGS. 2 and 7, a detachable and disposable heater adapter 100 has an input fitting 102 connected to output leg 66 of the discharge conduit 64 and has a heater output fitting 104. The heater adapter includes an intermediate enlarged body portion 106 forming an enlarged heater chamber 108 between the input and output fittings 102, 104. A cylindrical heater element 110, mounted to the heater adapter body, extends through an aperture 112 in the enlarged heater section 106 and terminates in an electrical connector 114 to which may be connected suitable power wires for the heater element and sensing wires for a thermocouple contained within the heater element 110. An annular heater baffle 119 projects radially inwardly from the interior surface of heater input fitting 102 at the junction of this fitting with the intermediate heater section 106. Heater chamber 108 has an increased diameter, being larger in cross-sectional area than the cross-sectional area of the input of the heater input fitting 102, and therefore, larger than the area of the passage through the heater baffle 120.

The illustrated heater configuration acts to further entrap water droplets and remove such large water droplets from the inhalation mixture. Baffle 120 acts to decrease the passage area, thus increasing its velocity. The baffle causes further entrapment of relatively large water particles which may then flow into the enlarged heater chamber 108. The flowing mixture passing through the enlarged heater chamber 108 decreases in velocity, thus providng a greater time for the desired heat exchange between the heater element and the mixture. In addition, the heater element raises the temperature of water that may collect in the bottom of the heater chamber, thus vaporizing water in the bottom of the heater chamber which then is again entrained as the desirably small sized droplets or vapor within the flowing mixture. The moisturized mixture having been heated in the heater chamber and further cleansed of larger water droplets, now may flow through the heater output fitting 104 and thence through an inhalation conduit (not shown) attached to the fitting 104 and connected to suitable breathing apparatus of the subject of the inhalation therapy.

Another unusual, surprising, and unexpected advantage of the described configuration is its quiet operation. Prior art nebulizers generate a significant amount of sound, which appears to emanate from the discharge tube. A large amount of noise also comes from the air entrainment ports (omitted in the configuration disclosed herein) of prior nebulizers, and thus increases background sound level in the area around prior nebulizers. Discharge tube sound is transmitted through the conduit connecting to the patient. It is found that the operation of the nebulizer described herein is as much as 50% quieter than commonly used prior art nebulizers. It is postulated that the significant decrease in noise of operation is due to the discharge of the liquid entraining mixture into the relatively large swirling chamber 90 and the structure of the nebulizer which directs this discharge into a relatively large diameter swirling path. Absence of open air entrance ports also contributes to the decrease in generated noise.

Preferably the container 10 is made as a one-piece molded vessel with the baffles 92 through 98 being tapered as illustrated in FIG. 3 solely for ease of molding. Lid 18 together with mixer body 20 are also molded as a single integral unit to which is then affixed to the jet nozzle 34 and deflector 46, the aspirator 42 and tube 44 connected between the aspirator and the container bottom. All parts are sterilized. Sterile water is introduced into the container to a suitable level below the container top (which may be one or two inches below the top) for an exemplary container that may be six inches from lid to bottom and three and a half inches in diameter at its lid.

There has been described an improved nebulizer employing a high-velocity oxygen stream that aspirates water for moisturization of the output, in which efficiency of water entrainment is significantly improved, in which the range of oxygen content of the output is extended downwardly, and in which a selected oxygen content of the output at a given input flow rate of oxygen can be maintained by independent adjustment of compressed air input. The arrangement provides a significant improvement by providing an increased moisture content of the output mixture and a significantly decreased amount of waste water.

The foregoing detailed description is to be clearly understood as given by way of illustration and example only, the spirit and scope of this invention being limited solely by the appended claims.

I claim:

1. A nebulizer for inhalation therapy comprising a mixer housing having a mixing chamber therein with an open end, said housing having first and second input ports, a venturi tube mounted in said open end, said venturi tube including an input end having an entrance surface tapering inwardly toward the axis of said tube and toward said open end, nozzle means in said chamber connected to said first port for projecting a first stream of high velocity oxygen from said first port along a first axis in said chamber, an aspirating conduit having an end in said chamber adjacent said nozzle means and adapted to be connected to a body of liquid for flowing liquid to said first stream at a point adjacent said nozzle means, thereby entraining liquid in said first stream, means for projecting a second stream of compressed air into said chamber in proximate relation to said nozzle means, deflector means in the path of said second stream and being configured and arranged for deflecting said second stream in a downwardly swirling path toward said entrance surface in a direction substantially parallel to said first stream and along a second axis adjacent the axis of said first stream, whereby said first and second streams are mixed with fluid in said chamber to provide a moisturized oxygen enriched air mixture, and, means for discharging said moisturized mixture from said chamber, said deflector means being oriented to direct said second stream along an axis intersecting said entrance surface of the venturi tube, said deflector means including an input fitting for said second stream having an axis transverse to said first mentioned axis, and means on said deflector means for redirecting air from said input fitting, said deflector means comprising a channel-shaped member having a web in proximate relation to said nozzle means and first and second side walls, said web and side walls being configured to redirect said second stream in said downwardly swirling path toward said entrance surface.

2. A nebulizer for inhalation therapy comprising a mixer housing having a mixing chamber therein, said mixer housing comprising a hollow body open at one end, and having first and second input ports, nozzle means in said chamber connected to said first port for projecting a first stream of high velocity oxygen from said first port along a first axis in said chamber, an aspirating conduit having an end in said chamber adjacent said nozzle means and adapted to be connected to a body of liquid for flowing liquid to said first stream at a point adjacent said nozzle means, thereby entraining liquid in said first stream, means for projecting a second stream of air in said chamber in a direction substantially parallel to said first stream and along a second axis adjacent the axis of said first stream, said means for projecting said second stream comprising a deflector on said nozzle means, an input fitting for said second stream having an axis transverse to said first-mentioned axis, and means on said deflector for redirecting air from said input fitting, said deflector comprising a channel-shaped member having a web fixed to said nozzle means and first and second side walls, and wherein said first and second streams are introduced to said chamber at points that are displaced from said one end, said first and second streams being directed to flow toward said one end, whereby said first and second streams are mixed with liquid in said chamber to provide a moisturized oxygen enriched air mixture, and means including a venturi tube mounted in said one end of the chamber for discharging said moisturized mixture from said chamber, said venturi tube including an input end having an entrance surface tapering inwardly toward the axis of said tube and toward said one end of said housing, said web and side walls of said deflector being configured to redirect said second stream in a downwardly swirling path toward said entrance surface, and wherein said second stream is directed along an axis intersecting said entrance surface.

3. A nebulizer for producing a mixture of oxygen enriched air and liquid for inhalation therapy comprising a container confining a body of liquid, a mixer body mounted to the container and comprising a mixer housing defining a mixing chamber, said mixer housing comprising a hollow body open at one end, a venturi tube mounted in said one end, said venturi tube including an input end having an entrance surface tapering inwardly toward the axis of said tube and toward said one end of said housing, nozzle means in said housing for projecting a first stream of gas at a high velocity along a first axis through said chamber, through said venturi tube and into said container, said first stream being introduced to said chamber at a point displaced from said one end and directed to flow toward said one end, aspirating means connected between a lower portion of said container and a point adjacent said nozzle means for flowing liquid from said container to said high velocity stream within said chamber, second gas input means for projecting a second stream of a second gas into said chamber along an axis transverse to said first axis, said second stream being introduced to said chamber at a point displaced from said one end, and deflector means in proximate relation to said second gas input means, said deflector means comprising a channel-shaped member having a web adjacent to said nozzle means and first and second side walls, said web and side walls being configured to redirect said second stream along a path generally parallel and in proximate relation to said first axis and in a downwardly swirling path toward said entrance surface, for producing a stream through said venturi tube comprising a moisturized mixture of liquid and said first and second gases.

4. A nebulizer for inhalation therapy comprising a mixer housing having a mixing chamber therein, said mixer housing comprising a hollow body open at one end, a venturi tube mounted in said one end, said venturi tube including an input end having an entrance surface tapering inwardly toward the axis of said tube and toward said one end of said housing, nozzle means in said housing for projecting a first stream of gas at a high velocity along a first axis through said chamber, through said venturi tube and into said container, said first stream being introduced to said chamber at a point displaced from said one end and directed to flow toward said one end, aspirating means connected between a lower portion of said container and a point adjacent said nozzle means for flowing liquid from said container to said high velocity stream within said chamber, second gas input means for projecting a second stream of a second gas into said chamber along an axis transverse to said first axis, and second stream being introduced into said chamber at a point displaced from said one end, and deflector means in proximate relation to said second gas input means, said deflector means comprising a channel-shaped member having a web adjacent to said nozzle means and first and second side walls, said web and side walls being configured to redirect said second stream along a path generally parallel and in proximate relation to said first axis and in a downwardly swirling path toward said entrance surface, for producing a stream through said venturi tube comprising a moisturized mixture of liquid and said first and second gases.

* * * * *